US006540688B1

United States Patent
Gingrich et al.

(10) Patent No.: US 6,540,688 B1
(45) Date of Patent: Apr. 1, 2003

(54) METHOD AND SYSTEM FOR ASSESSING COLLATERAL BLOOD FLOW TO A TISSUE REGION OF INTEREST

(75) Inventors: Matthew A. Gingrich, Boulder, CO (US); Jonas A. Pologe, Boulder, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 09/976,636

(22) Filed: Oct. 11, 2001

(51) Int. Cl.[7] .............................................. A61B 5/02
(52) U.S. Cl. ...................................... 600/504; 600/479
(58) Field of Search .............................. 600/504, 505, 600/507, 500, 481, 483, 485, 310, 473, 476, 477, 478, 479, 480

(56) References Cited

U.S. PATENT DOCUMENTS

| | | | |
|---|---|---|---|
| 3,796,213 A | 3/1974 | Stephens | 128/2.05 |
| 4,109,643 A | 8/1978 | Bond et al. | 128/2 |
| 4,204,545 A * | 5/1980 | Yamakoshi | 600/506 |
| 4,539,997 A | 9/1985 | Wesseling et al. | 128/667 |
| 4,562,843 A | 1/1986 | Djordjevich et al. | 128/672 |
| 4,869,253 A | 9/1989 | Craig, Jr. et al. | 128/633 |
| 5,050,613 A | 9/1991 | Newman et al. | 128/670 |
| 5,095,912 A | 3/1992 | Tomita | 128/672 |
| 5,297,548 A | 3/1994 | Pologe | 128/633 |
| 5,301,675 A | 4/1994 | Tomita | 128/672 |
| 5,503,148 A | 4/1996 | Pologe et al. | 128/633 |
| 5,671,750 A | 9/1997 | Shinoda | 128/672 |
| 5,715,826 A | 2/1998 | Horrocks et al. | 128/672 |
| 5,766,127 A | 6/1998 | Pologe et al. | 600/310 |
| 5,810,734 A | 9/1998 | Caro et al. | 600/485 |
| 5,833,618 A | 11/1998 | Caro et al. | 600/485 |
| 5,842,979 A | 12/1998 | Jarman | 600/322 |
| 5,862,805 A | 1/1999 | Nitzan | 128/898 |
| 5,891,024 A | 4/1999 | Jarman et al. | 600/323 |
| 5,913,826 A | 6/1999 | Blank | 600/500 |
| 5,934,277 A | 8/1999 | Mortz | 128/633 |

* cited by examiner

*Primary Examiner*—Max F. Hindenburg
*Assistant Examiner*—Navin Natnithithadha
(74) *Attorney, Agent, or Firm*—Marsh Fischmann & Breyfogle LLP (57) ABSTRACT

The present invention is directed to a method and system for use in assessing collateral blood flow to a tissue region of interest (ROI). The method includes the steps of obtaining a first pulsatility measurement and a second pulsatility measurement, wherein one of the pulsatility measurements is obtained with a plurality of arteries supplying blood to the tissue ROI and the other pulsatility measurement is obtained with at least a selected one of such arteries substantially occluded. The method further provides for use of the first and second pulsatility measurements to generate a collateral flow value useful to medical personnel as an objective measure in assessing collateral blood flow to a tissue ROI. The method may further include the step of obtaining a check pulsatility measurement after obtaining a first pulsatility measurement and prior to obtaining a second pulsatility measurement, wherein all of the plurality of the arteries are substantially occluded. The check procedure enhances the reliability of a second pulsatility measurement obtained when a selected one of the arteries is substantially occluded.

27 Claims, 8 Drawing Sheets

METHOD AND SYSTEM FOR ASSESSING COLLATERAL BLOOD FLOW TO A TISSUE REGION OF INTEREST

FIELD OF INVENTION

The present invention relates to a method and system for use in assessing collateral blood flow to a tissue region of interest, and is particularly apt for implementation in photoplethysmographic systems.

BACKGROUND OF THE INVENTION

The assessment of collateral blood flow to a specific bodily tissue region is of interest to medical personnel in a variety of situations. In this regard, medical personnel may be interested in assessing the adequacy of blood flow to a tissue region by a first supply artery when a second supply artery is not supplying blood thereto. Typically, such an assessment may be important when assessing the viability of relying upon a secondary artery to supply adequate blood flow to a tissue region of interest in the event the primary artery thereto is occluded or otherwise unable to deliver blood in conjunction with or pursuant to a given medical procedure.

By way of example, collateral blood flow to the hand through the radial artery is of interest when assessing the feasibility of utilizing the radial artery for cannulation or for harvesting graft tissue in conjunction with a given medical procedure (e.g., heart bypass surgery). To date, such assessments are often made via a manual test known as an "Allen's Test". In the Allen's Test, the patient tightly clenches a fist and then the clinician applies pressure to the radial and ulnar arteries to occlude further blood flow to the hand under test. The patient then opens the clenched fist while pressure is maintained over both arteries. The hand appears blanched and free of blood. Pressure on the ulnar artery is released and the time required for blood flow to reach each finger is noted by measuring the time required for the color in the fingertips to change back from the blanched state to the normal blood filled state. The time required for color to return to the fingers is inversely proportional to the adequacy of the collateral blood flow through the ulnar artery.

As may be appreciated, use of the Allen's Test to assess collateral blood flow involves a significant degree of subjectivity. The present inventors have recognized the desirability of providing a method and system that provides a more objective measure for assessing collateral blood flow.

SUMMARY OF THE INVENTION

In view of the foregoing, a general objective of the present invention is to provide an improved approach for assessing collateral blood flow to a tissue region of interest.

A more specific objective of the present invention is to provide an approach for collateral blood flow assessment that is both quantitative and more reliable than currently utilized techniques.

Another objective of the present invention is to provide a non-invasive and at least partially-automated approach for collateral blood flow assessment.

An additional objective of the present invention is to provide an improved collateral blood flow assessment approach that may be readily implemented in photoplethysmographic systems.

The above objectives and additional advantages are realized in an inventive method that includes a first step of obtaining at least a first pulsatility measurement (FPM) and a second pulsatility measurement (SPM) indicative of the volume of blood flow to a tissue region of interest (ROI). For purposes hereof, the term "pulsatility measurement" encompasses any technique employable to obtain a measure, relative or otherwise, of the perfusion of a tissue ROI of a patient or test subject. In the inventive method, one of the FPM and SPM is obtained with a plurality of arteries supplying blood to the tissue region of interest, while the other of the FPM and SPM is obtained with at least a selected one of said plurality of said arteries substantially occluded. Following the obtainment of the first and second pulsatility measurements, the method further includes the step of employing such measurements to obtain a collateral blood flow value (CFV) employable by medical personnel to quantify the acceptability of collateral blood flow to the tissue ROI.

Pulsatility measurements may be obtained by passing at least a first light signal through the tissue ROI and detecting the intensity of the transmitted signal. The detected signal may be utilized to compute (e.g. via a processor) the first pulsatility measurement and second pulsatility measurement. For example, where a single light signal is utilized the pulsatility measurements may simply entail the calculation of the percent modulation of the transmitted signal. In another approach, the pulsatility measurements may be perfusion index values obtained in a manner taught by U.S. Pat. No. 5,766,127, hereby incorporated by reference. As will be appreciated, the present invention may be readily implemented in and is otherwise particularly apt for use in a photoplethysmographic system.

In a further aspect, the inventive method may comprise the step of storing the first and second pulsatility measurements (e.g. in memory in a microprocessor based system) for use in obtaining the CFV. By way of example, the CFV may be a computed ratio of the FPM and SPM, expressed as a percentage. Further, the inventive method may comprise the additional step of outputting the CFV to a user via a user interface, e.g. via display and/or audible signals.

The first pulsatility measurement and second pulsatility measurement should be obtained during non-overlapping time periods. Further the inventive method may comprise the step of prompting a user at the beginning and/or ending of the time period associated with the obtainment of the FPM and/or the time period associated with obtainment of the SPM. Such prompting facilitates the establishment of the desired arterial occlusion or non-occlusion for the given pulsatility measurement. By way of example, prompts may be provided in the form of display and/or audible signals. Further, the prompts may comprise instruction information to guide a user through the occlusion steps.

In an additional aspect, obtaining the first pulsatility measurement may entail the steps of obtaining a plurality of first pulsatility values (FPVs) and determining the FPM utilizing the first plurality of FPVs. The method may further include the substep of comparing the plurality of FPVs to a first reference range (e.g. such range being set to be ± a predetermined percentage of a mean value of the first plurality of first pulsatility values), wherein if/when all of the plurality of FPVs are within the first reference range obtainment of the FPM may be completed. In the later regard, a mean value of the plurality of FPVs may be used as the FPM. In the event that a given plurality of FPVs do not fall within the first reference range, the method may further provide for the obtainment of a new plurality of FPVs and subsequent comparison thereof to a corresponding first reference range. Such substeps may be repeated until a given plurality of FPVs fall within a corresponding first reference range. As may be appreciated, the obtainment of a plurality of FPVs and the comparison thereof to a first reference range yields enhanced accuracy in relation to the FPM based thereupon. In turn, overall reliability is increased.

Correspondingly, the obtainment of a second pulsatility measurement may entail the obtainment of a plurality of second pulsatility values (SPVs) and the comparison of the plurality of SPVs to a second reference range (e.g. such range being set to be ± a predetermined percentage of a mean value of the plurality of SPVs). When all of the SPVs are within the second reference range obtainment of the SPM may be completed (e.g., by using a mean value of the SPVs). In the event a given plurality of SPVs are not all within a second reference range a new plurality of SPVs may be obtained and compared to a corresponding second reference range. Such substeps may be repeated until a given plurality of SPVs fall within a corresponding second reference range. The obtainment and noted use of a plurality of SPVs yields enhanced accuracy of an SPM based thereupon, and improves overall reliability.

In addition the present invention may include a check procedure for further enhancing the accuracy and reliability of the measurements. In particular, a check pulsatility measurement (CPM) may be obtained after FPM obtainment and prior to SPM obtainment, wherein the CPM is obtained with all of the plurality of arteries supplying the ROI substantially occluded. The CPM may be compared to a check reference range, wherein if the CPM is within the check reference range the SPM may be obtained. By way of example, when the FPM is obtained with all of the plurality of arteries to an ROI open, then if the CPM is within a predetermined small percentage (e.g., 0 to 5%) of the FPM, the SPM may be obtained. In the event the CPM is not within the check reference range a user prompt may be provided. The prompt may be in the form of a displayed or audible signal, and may include remedial action information. Such an approach serves to ensure that the artery which is intended to be occluded during obtainment of an SPM is in fact sufficiently occluded.

The present invention is particularly apt for implementation in a photoplethysmographic system. In our current embodiment of this invention a photoplethysmographic sensor provides an output signal indicative of the amount of a light transmitted through a tissue region of interest. The system includes a means for utilizing the sensor output signal to obtain first and second pulsatility measurements, e.g. an FPM and SPM as noted above. The system calculates the collateral flow from the FPM and SPM, utilizing the CPM procedure as noted above.

The system may be provided for operation in at least two modes, wherein in the first mode of operation the system measures at least one blood analyte concentration value (e.g. blood oxygenation levels), and wherein in the second mode of operation the system provides a CFV value as noted above. In this regard, the system may further include a user interface selection means for allowing a user to select system operation in the first mode or second mode. As may be appreciated, the user interface means may be further operable to output a CFV to a user via display/audible signals. In the later regard, the system may be designed so that the output mode is also selectable by a user.

In conjunction with the inventive system, the pulsatility means may be operable to automatically obtain a first plurality of pulsatility values for automatic computation of an FPM, and to automatically obtain a second plurality pulsatility values for automatic computation of an SPM. Automatic computation of the FPM and SPM may entail the computation of mean values and comparison of individual pulsatility measurements thereto, as discussed above.

The pulsatility means may further provide for the automatic obtainment of a check pulsatility measurement, or CPM as noted above, wherein an SPM is not obtained until a CPM is obtained within a predetermined range. In the event a CPM is not obtained within the check reference range, the user interface means may be provided to provide remedial information to a user. By way of example, such remedial information may instruct a user to relocate the point of pressure application to the arteries supplying blood to the tissue region of interest.

The user interface means of the inventive system may further provide for user prompting in relation to the sequence of occluding and opening the plurality of arteries supplying blood to a given tissue region of interest. More particularly, such prompting may comprise audible/visual output information to assist/instruct medical personnel in occluding the correct arteries. Such prompting may be further provided in a manner so that each occlusion/opening step is only undertaken after a desired degree of accuracy and/or stability is achieved with respect to the FPM, CPM and SPM in a course of a given collateral blood flow test procedure.

Additional aspects and advantages of the present invention will be apparent to those skilled in the art upon review of the further description that follows.

DETAILED DESCRIPTION

Figure 1:
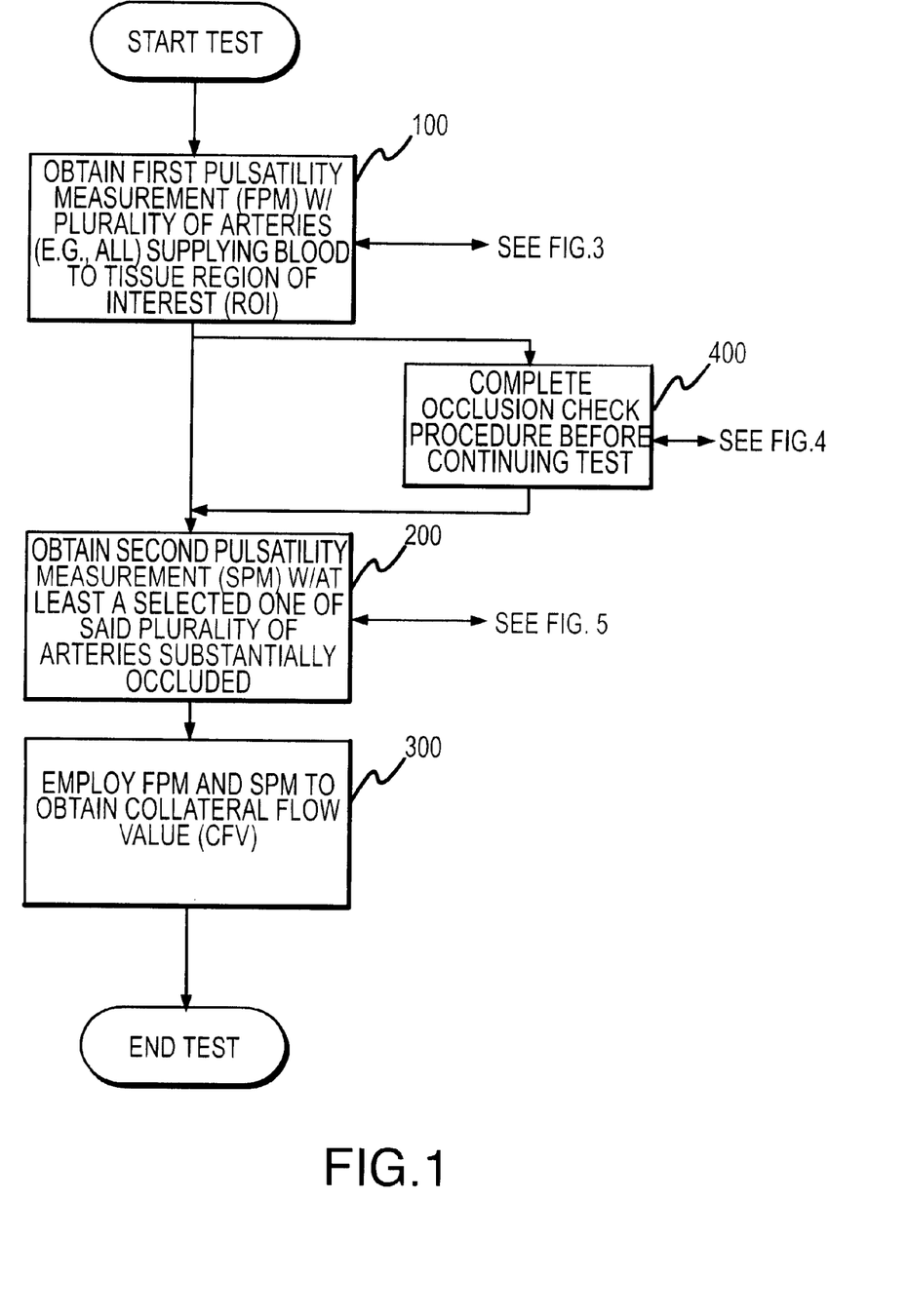
FIG. 1 illustrates steps of the inventive method comprising the present invention.

FIG. 1 illustrates basic steps of an inventive method for measuring collateral blood flow to a tissue region of interest (ROI).

In an exemplary application, the inventive method may be employed to assess the adequacy of collateral blood flow to the hand. At the outset of the procedure a first pulsatility measurement (FPM) may be obtained at the ROI while a plurality of arteries are supplying blood thereto (step 100). As previously noted, a pulsatility measurement may entail any technique that provides a measure, relative or absolute, of the perfusion of a tissue ROI. The obtainment of an FPM provides a baseline value for subsequent use. In the noted exemplary application, the ulnar and radial arteries may be left open, or non-occluded, while the FPM is obtained.

After obtaining an FPM, a second pulsatility measurement (SPM) may be obtained at the ROI with at least a selected one of the plurality of arteries supplying blood to the tissue ROI substantially occluded (step 200). In the noted exemplary application, this may entail the application of pressure to the radial artery so as to substantially occlude all blood flow to the hand.

After obtaining the FPM and SPM, the two measurements may be utilized together to obtain a collateral flow value (CFV) which provides an indication of the adequacy of collateral blood flow to the tissue ROI (step 300). In one arrangement, the CFV may simply be a ratio of SPM/FPM, expressed as a percentage. In the noted example, a CFV of 20% would indicate that the ulnar artery supplies one-fifth of the total normal blood flow supplied to a hand by the ulnar and radial arteries together. For hand applications, the CFV may be employed by medical personnel to assess the viability of employing the radial artery for cannulation or for harvesting for use in a coronary bypass procedure.

As noted above, the obtainment of an SPM entails the occlusion of one of the plurality of arteries supplying blood to a tissue ROI. In order to enhance the accuracy of the SPM obtained, the illustrated process may further include a complete occlusion check procedure after the obtainment of the FPM and prior to the obtainment of an SPM (step 400). As will be further described, the occlusion check procedure may entail the obtainment of a check pulsatility measurement (CPM) while substantially occluding all of the plurality of arteries supplying blood to the tissue ROI (e.g., via the application of pressure thereto). In the previous example, such a procedure would therefore require the obtainment a check pulsatility measurement (CPM) while both the ulnar and radial arteries are substantially occluded. Such CPM may be employed to confirm that the ulnar and radial arteries have been sufficiently occluded before obtaining the SPM measurement.

A description of various embodiments for completing steps 100, 200, 300 and 400 will be provided below. Before that, however, it should be realized that the present invention is particularly apt for implementation in a photoplethysmographic system. In that regard, reference will now be made to FIG. 2 which illustrates an exemplary system embodiment 10.

Figure 2:
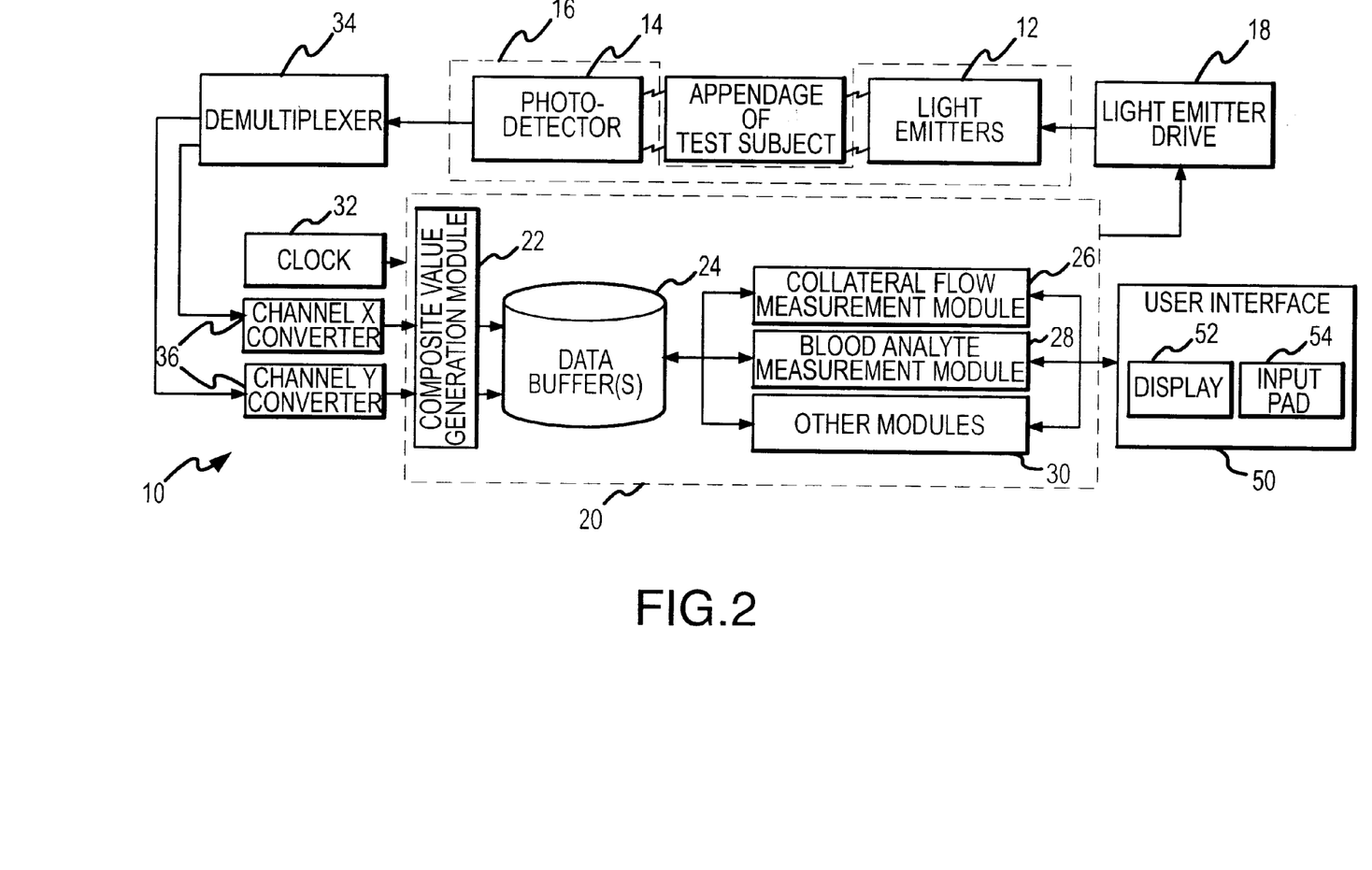
FIG. 2 illustrates an exemplary photoplethysmographic system that may implement the present invention.

As shown, the system embodiment 10 comprises light emitters 12 and a photodetector 14. Emitters 12 and photodetector 14 may be incorporated into a sensor 16 adapted for removable attachment to an appendage of a test subject. By way of example, and in relation to the exemplary application of the present invention noted above, such appendage may be a finger or thumb. The thumb would typically be used in a test of the patency of blood flow to the hand due to its position at the end of the ulnar arch, the vessel that supplies blood to the fingers via the ulnar artery when the radial artery is occluded. By checking for blood flow at the thumb one is fairly well assured that the ulnar artery is properly supplying blood to all the fingers of the hand.

In use, the sensor 16 is positioned to direct light signals emitted by emitters 12 onto one side of the appendage. Photodetector 14 is positioned on the opposite side of the appendage to receive light that is transmitted through the tissue and to produce an output signal responsive to the intensity of the transmitted light signal(s). In a typical photoplethysmographic system emitters 12 may be provided to emit light signals at two different center frequencies for blood analyte measurements, e.g., red light signals and infrared light signals. The emitters 12 may be interconnected to a light emitting drive 18 that is controlled by a processor 20 with an interconnected clock 32. The light signals emitted by emitters 12 may be multiplexed according to a predetermined scheme (e.g., time-division multiplexed, frequency division multiplexed, code-division multiplex, etc.). In turn, a demultiplexer 34 may be provided to separate the detector output signal into signal portions corresponding with each of the emitted light signals in separate processing channels, e.g., channels X and Y, respectively. Signal converters 36 may be provided in each of the channels, X, Y, with current-to-voltage amplifiers, analog-to-digital converters and other components for digitizing the signals for processing by the processor 20.

Processor unit 20 may comprise a front end module 22 that receives digitized detector signal values in channels X and/or Y and generates a series of composite first (e.g., infrared) and/or second (e.g., red) signal values. Processor unit 20 may further comprise one or more data storage buffers 24 to store first and/or second signal values received from module 22, as well as additional values computed by various computation modules comprising processor 20. In the latter regard, such computation modules may include a collateral flow measurement module 26 for use in conjunction with the present invention, a blood analyte measurement module 28 for providing blood analyte information (e.g., blood oxygen saturation values), and other modules 30 for providing other information derivable from the data stored at buffer(s) 24.

Blood analyte measurement module 28 may access first and second signal values in buffer 24 to compute differential absorption data sets (e.g., differential infrared and differential red data sets) from which blood analyte values may be determined. By way of example, each blood analyte value may be defined to correspond with a best-fit function determined for a plurality of data sets utilized in a given measurement. In this regard, blood analyte computation measurement module 28 may incorporate known process functionalities, including those taught by U.S. Pat. Nos. 5,503,148; 5,842,979; 5,891,024 and 5,934,277.

The collateral flow measurement module 26 may provide functionalities to facilitate the method discussed in relation to FIG. 1 and the related embodiments further described below. In this regard, the collateral flow measurement module 26 may access the data stored at buffer(s) 24 to automatically obtain pulsatility measurements. Such pulsatility measurements may be calculated using the data corresponding with the first signal and/or second signal noted above. By way of example, signal data corresponding with only one of the emitters 12 may be obtained and utilized to calculate percent modulation values that provide an indication of the relative perfusion of a tissue ROI. In another approach, signal data corresponding with two or more emitters 12 may be obtained and utilized to obtain perfusion indications as taught in U.S. Pat. No. 5,766,127. Further, the collateral flow measurement module 26 may utilize the pulsatility measurements to automatically control a test procedure, as described below, and to calculate a collateral flow value (CFV) as discussed herein.

As illustrated, system 10 further includes a user interface 50 for providing outputs of measurement information determined by modules 26, 28 and 30 of processor 20. By way of example, the user interface 50 may comprise an alphanumeric display 52 for displaying the measurement information and for otherwise prompting/advising a user in relation to operations of the system 10. Alternatively or additionally, user interface 50 may comprise audible output/prompting capabilities. Further, user interface system may include an input device 54, such as a user input pad, mouse or touchscreen for allowing a user to control various operations of the system 10. By way of example, user interface 50 and processor unit 20 may be provided so that a user may select a given desired mode of operation of system 10, e.g., wherein in a first mode a collateral blood flow test procedure is carried out utilizing module 26, and wherein in a second mode of operation normal photoplethysmographic measurements, such as the measurement of oxygen saturation, may be made utilizing module 28.

Figure 3:
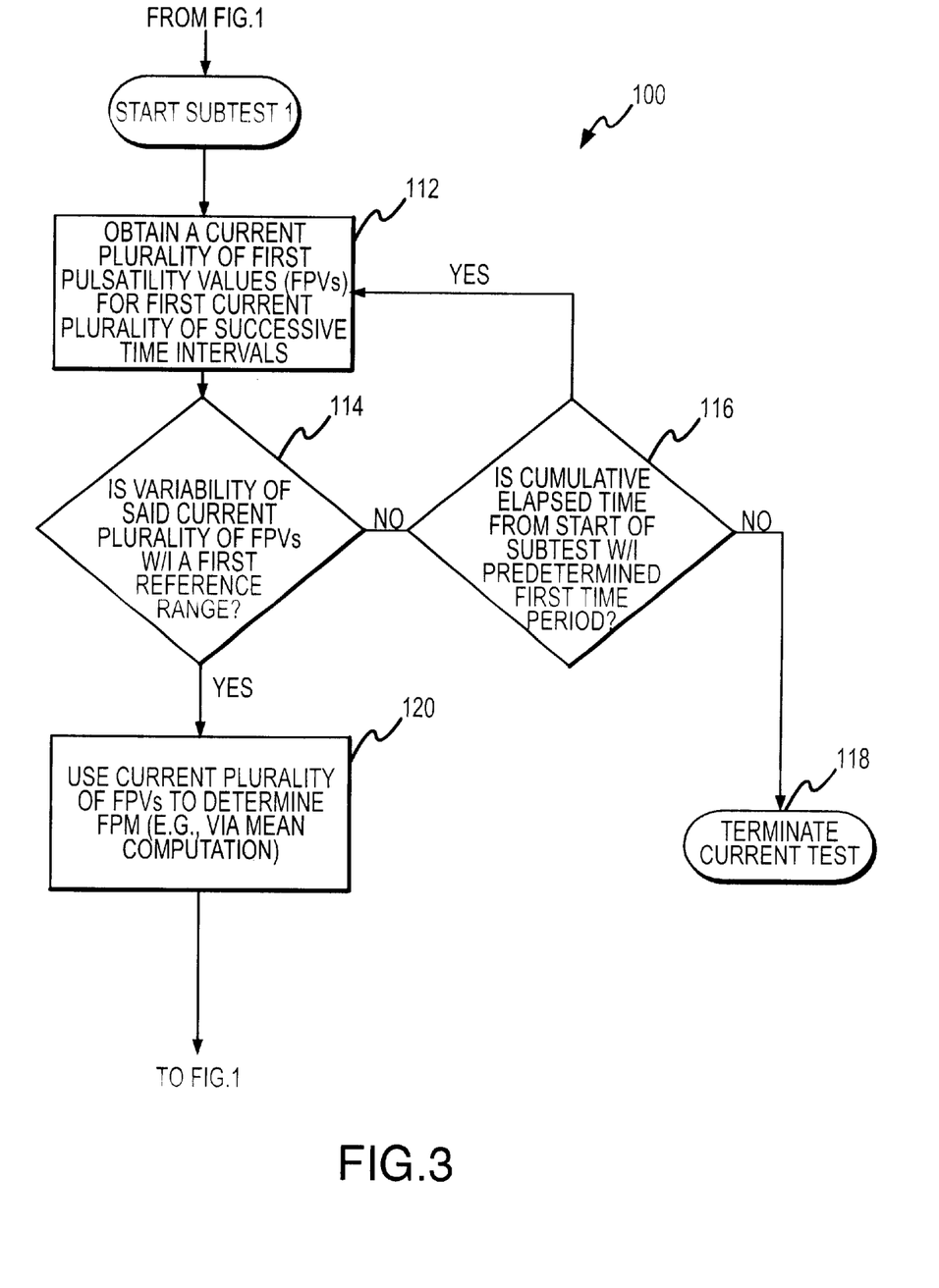
FIG. 3 illustrates one embodiment for completing step 100 of the method illustrated in FIG. 1.
Figure 4:
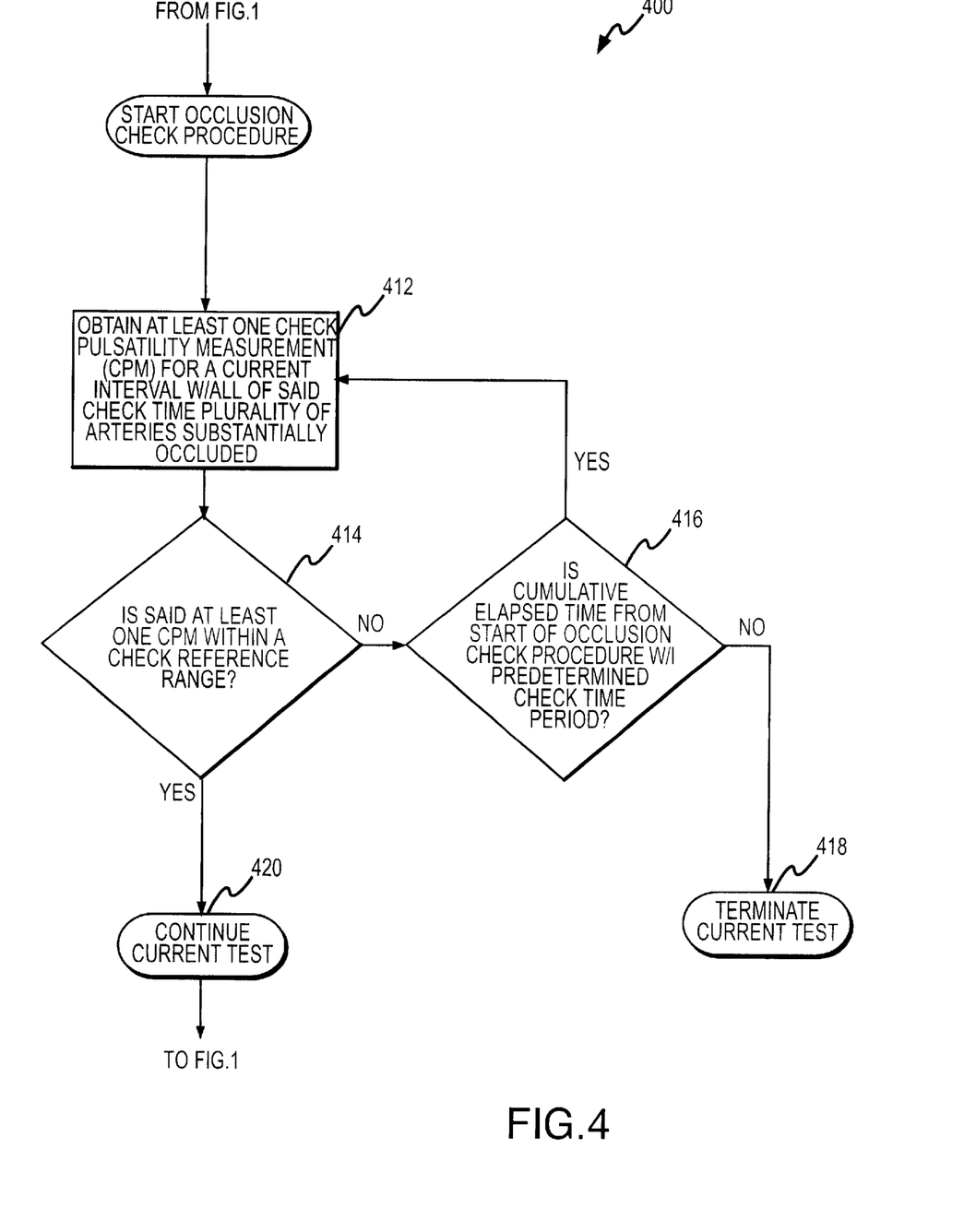
FIG. 4 illustrates one embodiment for completing step 400 of the method illustrated in FIG. 1.
Figure 5:
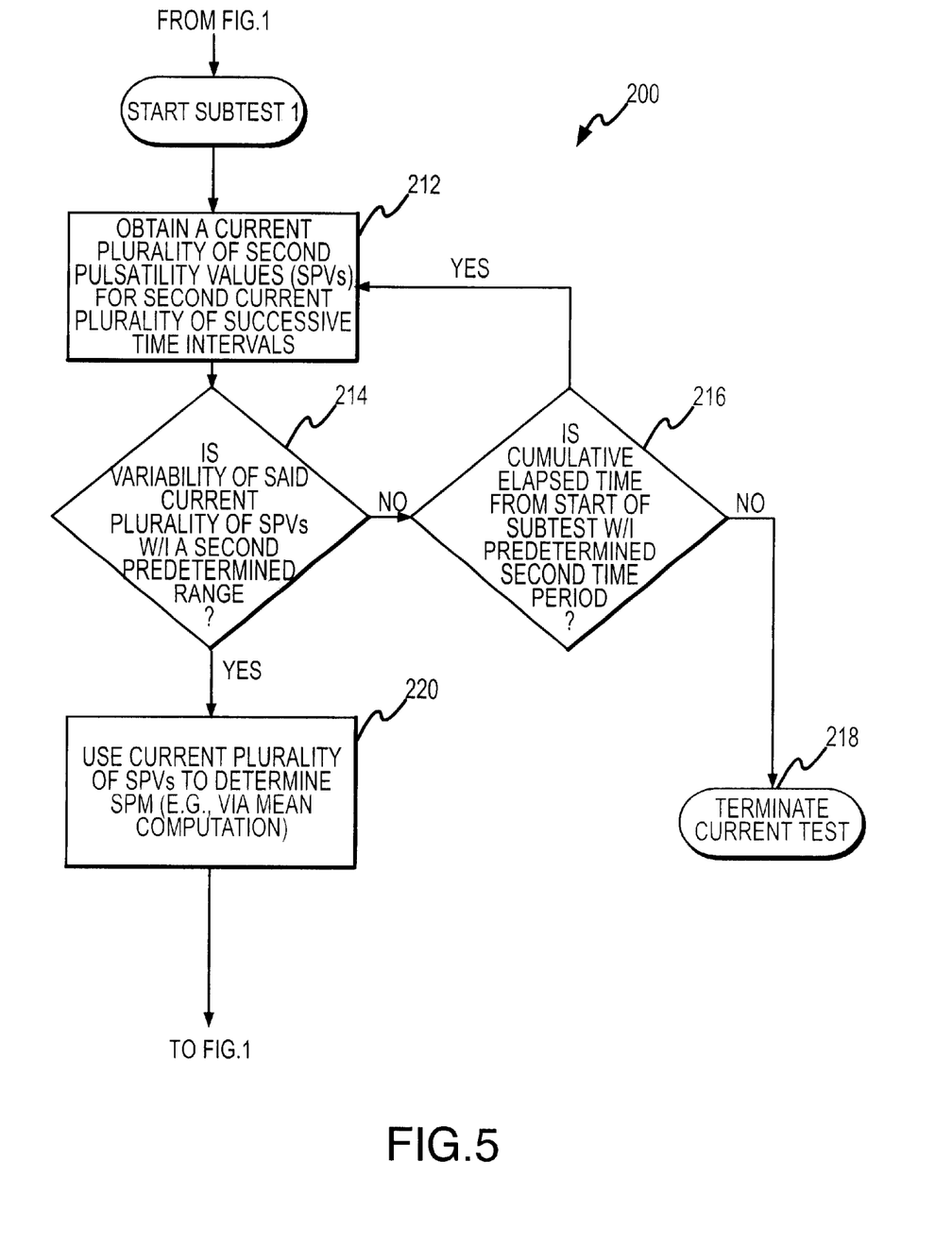
FIG. 5 illustrates one embodiment for completing step 200 of the method illustrated in FIG. 1.

Referring now to FIGS. 3, 4 and 5 various embodiments for the process steps identified in FIG. 1 will now be described. As shown in FIG. 3, the obtainment of a first pulsatility measurement (FPM) in step 100 may entail the substep of obtaining a plurality of pulsatility values (FPVs) for each of a corresponding current plurality of successive time intervals during which a plurality of arteries supplying the tissue ROI are open (substep 112). The obtainment of a plurality of FPVs allows for an assessment of the stability thereof prior to use in the determination of an FPM, thereby enhancing accuracy and reliability. To assess such stability, the variability of the FPVs may be evaluated in relation to a predetermined range (substep 114). More particularly, in one approach each of the plurality of FPVs may be compared to a mean value for that plurality, wherein if each or a predetermined portion of the plurality of FPVs, for example perhaps the last 5 calculated FPVs, is within a predetermined percentage of the mean value the process may continue. If such stability is not obtained, substeps 112 and 114 may be successively repeated to obtain and assess a new plurality of FPVs corresponding with a new plurality of successive time intervals (e.g., partially overlapping with or totally different from the initial considered plurality of FPVs and corresponding intervals).

In order to ensure that an overall collateral flow test procedure does not extend beyond a preset amount of time, the process may also include the application of a time limit for completing step 100. As illustrated in FIG. 3, this may entail the added step of determining whether or not the required stability in FPV readings has been realized within a predetermined time period (substep 116). If not, the current test procedure may be automatically terminated (substep 118). In the event the required stability is established within the allotted time, the corresponding plurality of FPVs may be employed to determine the baseline FPM (substep 120). For example, the FPM may be established equal to the mean value computed plurality of FPVs measured in substep 112 and accepted in substep 114.

As shown in FIG. 4, the optional complete occlusion check procedure of step 400 may entail the initial substep of obtaining a check pulsatility measurement (CPM) corresponding with at least one current time interval during which all of the arteries supplying blood to the tissue ROI are substantially occluded (substep 412). The obtainment of a CPM allows for an assessment of how well, or the degree to which the arteries have been occluded, thereby enhancing the accuracy and reliability of the SPM to be obtained in step 200. To assess the degree of occlusion, at least one pulsatility value may be obtained and compared to a predetermined level (substep 414). By way of example, the CPM may be compared to the baseline FPM, wherein if the CPM is less than a predetermined percentage (e.g., less than about 5%) of the FPM the process may continue (substep 420). If such degree of occlusion is not obtained, substeps 412 and 414 may be successively repeated to obtain and assess CPMs corresponding with one or more successive time intervals. Again, in order to ensure that an overall collateral flow test procedure does not extend beyond a preset amount of time, the process may also include the application of a time limit for completing step 400. As shown in FIG. 4, this may entail the added step of determining whether or not the required degree of occlusion has been realized within a predetermined time period (substep 416). If not, the current test procedure may be automatically terminated (substep 418). In the event that the required occlusion is established, the test may continue (substep 420).

FIG. 5 reflects an embodiment for obtaining the second pulsatility measurement (SPM) of step 200 and may entail the initial substep of obtaining a plurality of pulsatility values (SPVs) for each of a corresponding current plurality of successive time intervals during which at least one of the plurality of arteries supplying a tissue ROI is substantially occluded (substep 212). The obtainment of a plurality of SPVs allows for an assessment of the stability prior to use in the determination an SPM, thereby enhancing accuracy and reliability. To assess such stability, the variability of the SPVs may be evaluated in relation to a predetermined range (substep 214). More particularly, in one approach, each of the plurality of SPVs may be compared to a mean value for that plurality, wherein if each or a predetermined portion of the plurality of SPVs is within a predetermined percentage of the mean value the process may continue. If such stability is not obtained, substeps 212 and 214 may be successively repeated to obtain and assess new plurality of SPVs corresponding with a new plurality of successive time intervals (e.g., partially overlapping with or totally different from the initial considered plurality of SPVs and corresponding intervals). Again, in order to ensure that an overall collateral flow test procedure does not extend beyond a preset amount of time, the process may also include the application of a time limit for completing step 200. As indicated in FIG. 5, this may entail the added step of determining whether or not the required stability in SPV readings has been realized within a predetermined time period (substep 216). If not, the current test procedure may be automatically terminated (substep 218). In the event the required stability is established, the corresponding plurality of SPVs may be employed to determine the FPM (substep 220). For example, the SPM may be established equal to the mean value computed with respect to the plurality of SPVs measured in substep 212 and accepted in substep 214.

As noted above in relation to FIG. 1, the FPM and SPM obtained in conjunction with a given collateral flow test procedure may be employed together to obtain a collateral flow value (CFV). In one approach, the CFV value may simply be a ratio of the SPM to the FPM, expressed as a percentage and output to a user.

The exemplary photoplethysmographic system 10 shown in FIG. 2 may be employed for implementation of the embodiments described above in relation to FIGS. 3, 4 and 5. For such purposes, the collateral flow measurement module 26 of processor 20 and the user interface 50 may be provided to facilitate and control a collateral flow test procedure. In that regard, reference is now made to FIGS. 6A and 6B which illustrate processor and use interface functionalities that may be implemented. As shown, to initiate a given collateral flow test procedure utilizing system 10, user interface 50 may provide for a user selection input. For example, a plurality of operational modes may be presented in a menu fashion at display 52 for user selection utilizing input pad 54. Such plurality of modes may include a collateral flow test mode and a blood analyte measurement mode.

Figure 6A:
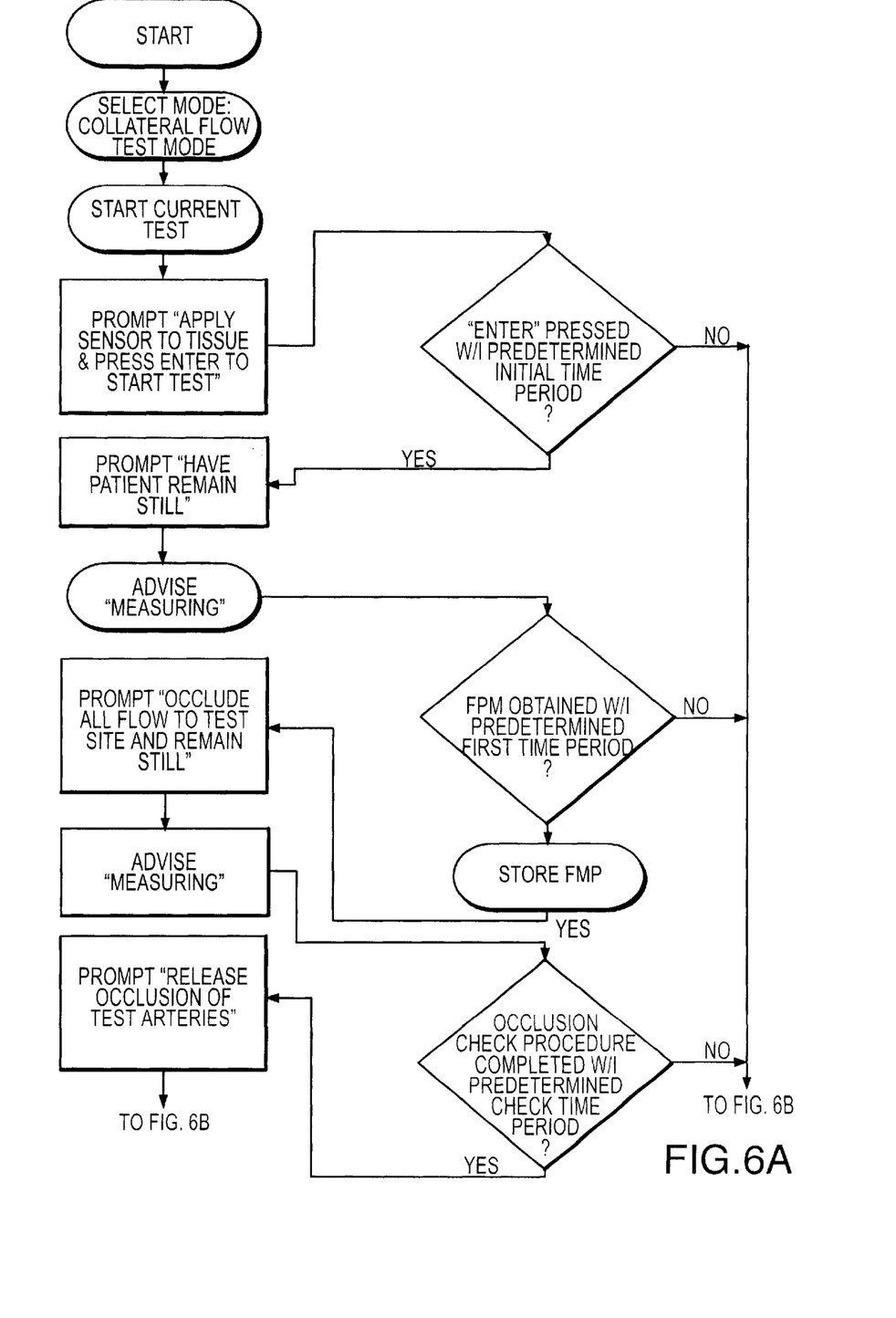
FIGS. 6A and 6B illustrate one embodiment of a user interface process employable in conjunction with the present invention.
Figure 6B:
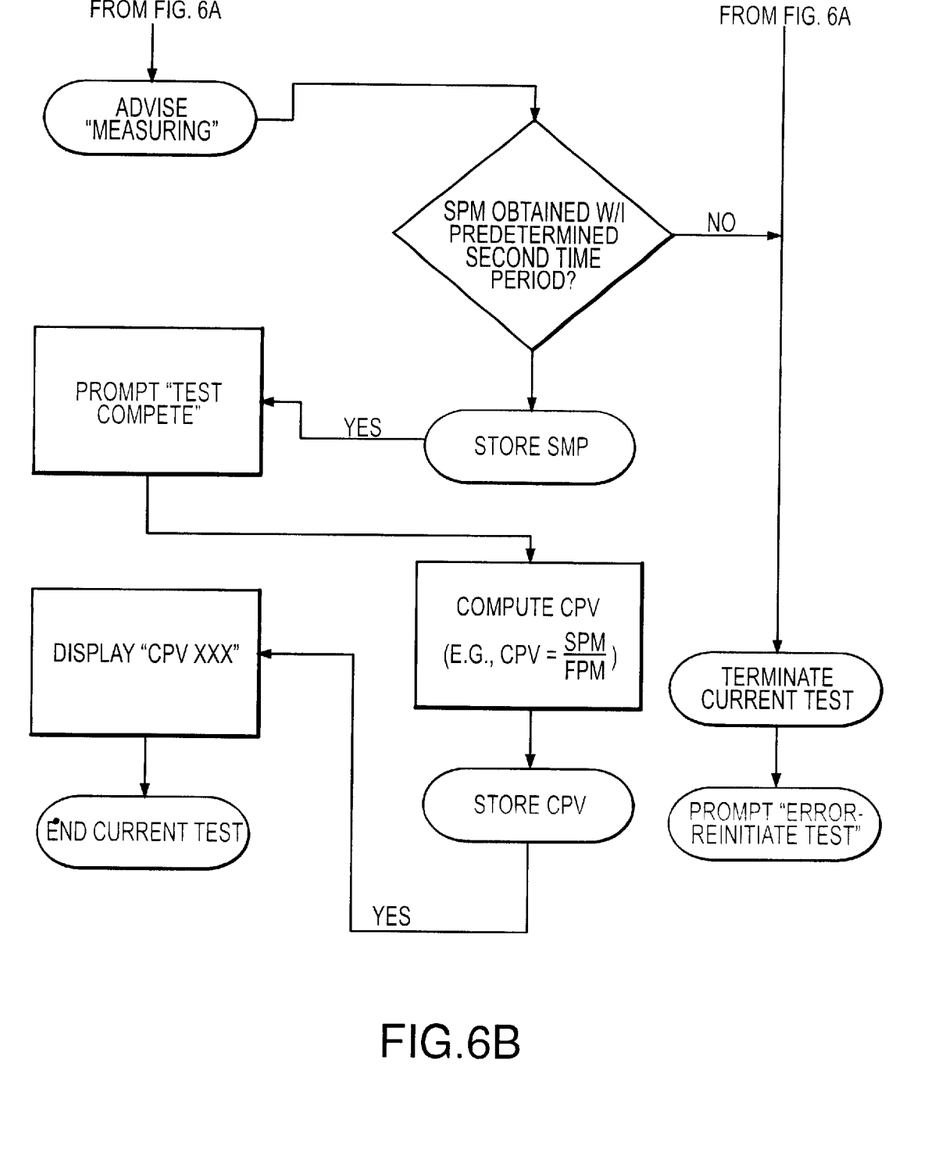

Upon selection of the collateral flow test mode, the collateral flow measurement module 26 may control system 10, and in particular user interface 50, to complete a test procedure as described below. In particular, the user interface 50 may prompt the user to "APPLY SENSOR TO TISSUE & PRESS ENTER TO START TEST". Such prompt may be provided in the form of a visual output at display 52 and/or may be audibly provided. Thereafter, a user would attach a sensor 16 to a tissue ROI and press an "ENTER" button at the input pad 54 of the user interface 50. If a user has not pressed the "ENTER" button within a predetermined initial time period the test procedure may be automatically terminated. In the event that the user timely presses the "ENTER" button, the user interface 50 may then prompt the user to "HAVE PATIENT REMAIN STILL", and subsequently the user interface 50 may advise the user that system 10 is "MEASURING".

At this point system 10 may be completing step 100 in accordance with the embodiment of FIG. 3 to obtain an FPM. In the system configuration of FIG. 2, this may entail use of one or more light signals from emitters 12. As noted above in relation to step 116, the illustrated process may provide for a determination of whether or not an FPM is obtained within a predetermined time period. If not, the current test procedure may be automatically terminated and the user interface 50 may advise "ERROR—REINITIATE TEST". If an FPM is obtained with the required time period the FPM may be stored in processor 20 for subsequent use.

Thereafter, the user interface 50 may prompt a user to "OCCLUDE ALL FLOW TO TEST SITE AND REMAIN STILL", and user interface 50 may subsequently advise that system 10 is again "MEASURING". In the system configuration of FIG. 2, this may entail use of one or more light signals from emitters 12. At this point, system 10 may complete step 400 in accordance with the embodiment discussed above in relation to FIG. 4. In relation to step 416 noted above, the illustrated process may further provide for a determination of whether or not the occlusion check procedure has been successfully completed within a predetermined time period. If not, the current test procedure may be automatically terminated and user interface may advise "ERROR—REINITIATE TEST". If the current test is completed within the required time period user interface 50 may then prompt a user to "RELEASE OCCLUSION OF TEST ARTERIES", and user interface 50 may subsequently advise user that the system is again "MEASURING".

At this point system 10 may be completing step 200 in accordance with the embodiments of FIG. 5 to obtain an SPM. In the system configuration of FIG. 2, this may entail use of one or more light signals from emitters 12. As noted in relation to step 216 above, the illustrated process may provide for a determination of whether or not an SPM is obtained within a predetermined time period. If not, the current test procedure may be automatically terminated and user interface 50 may advise "ERROR—REINITIATE TEST". If an SPM is obtained with the required time, the SPM may be stored at processor 20. User interface 50 may then advise "TEST COMPLETE", and system 10 may complete step 300 of the process sequence shown in FIG. 1. In particular, the CFV value may be determined by computing the ratio of the SPM to FPM. Thereafter, the CFV value may be displayed at user interface 50 to complete the collateral flow test procedure. Subsequently, medical personal may employ the CFV valve to assess the collateral blood flow to the tissue ROI, e.g. to assess the viability of using the radial artery for cannulation or for harvesting graft tissue.

Figure 7:
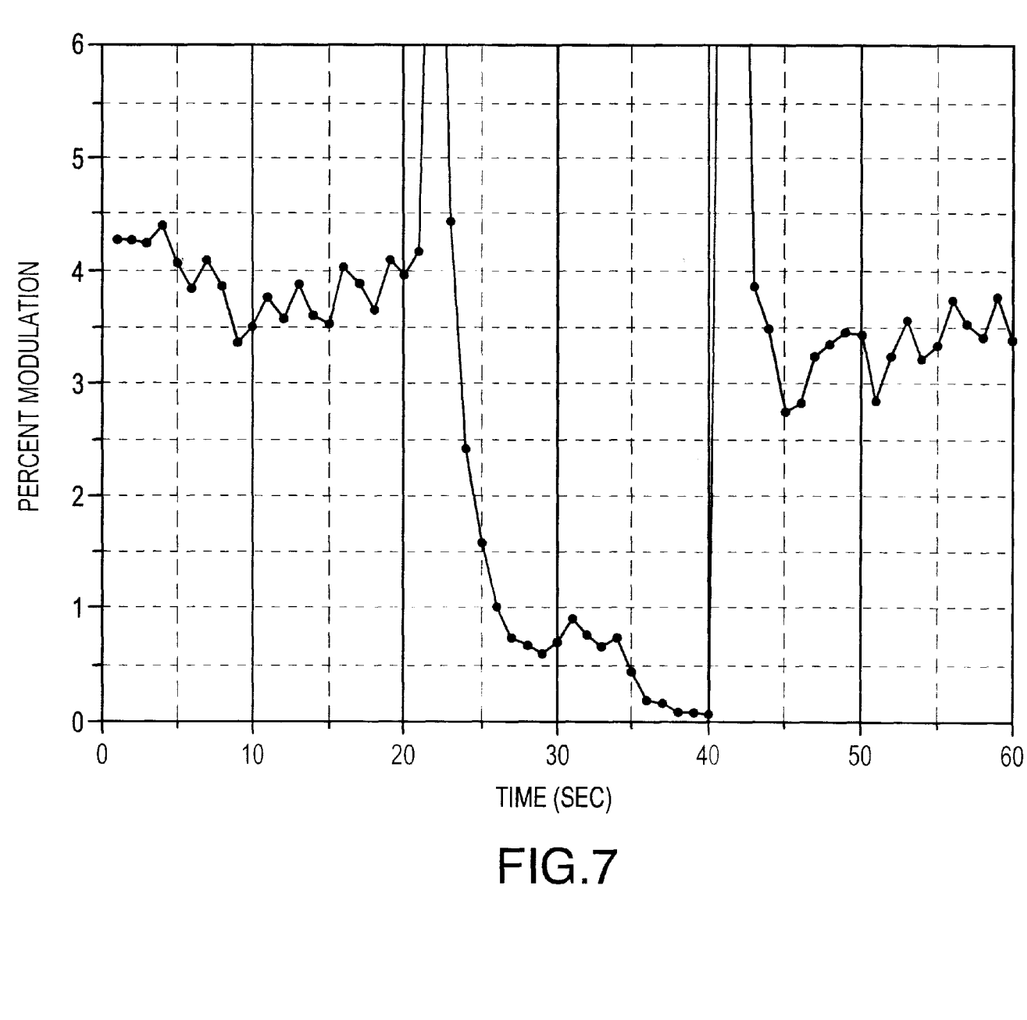
FIG. 7 illustrates a graphical depiction of pulsatility measurements obtained in conjunction with an exemplary use of the present invention.

Reference is now made to FIG. 7 which illustrates a sequence of pulsatility measurements, each expressed in the form of percent modulation, obtained during an exemplary collateral blood flow test procedure (e.g. to assess collateral flow to the hand). As shown, during an initial 20 second period the arteries supplying blood to the ROI are left open while an FPM is obtained, per step 100. Of note, a plurality of FPVs (e.g. ten) are obtained between 10 and 20 seconds that are each within a predetermined percentage of mean value thereof (e.g. about 3.8). In turn, all arteries to the ROI are occluded between 20 and 40 seconds while a CPM is obtained, per step 400 above. More particularly, a series of CPMs are obtained, wherein the final one of several CPMs obtained is within a predetermined percentage of the FPM (e.g. less than about 2.5% of the 3.8 FPM value). Next, during the 40 to 60 second time period at least one of the arteries to the ROI is opened (i.e. to assess collateral blood flow therethrough) and the other arteries to the ROI are left occluded while an SPM is obtained per step 200 above. For example, in the noted application, the radial artery occlusion is maintained while pressure on the ulnar artery is released. As shown, a plurality of SPVs (e.g. ten) are obtained between 50 and 60 seconds that are each within a predetermined percentage of a mean value thereof (e.g. about 3.4). As such, the mean value establishes the SPM. The obtained FPM and SPM result in a CFV valve of about 90.7% (e.g. the FPM/SPM expressed as a percentage).

The description provided above is to facilitate an understanding of one application of the present invention. Modifications and extensions of the invention will be apparent to those skilled in the art and are intended to be, within the scope of the present invention as defined by the claims which follow.

What is claimed is:

1. A method for use in assessing collateral blood flow to a tissue region of interest, comprising:

obtaining at least a first pulsatility measurement and a second pulsatility measurement indicative of the volume of blood flow to a tissue region of interest, wherein one of said first and second pulsatility measurements is obtained with a plurality of arteries supplying blood to the tissue region of interest, and wherein the other of said first and second pulsatility measurements is obtained with at least one of said plurality of arteries substantially occluded; and, employing said first pulsatility measurement and said second pulsatility measurement to obtain a value employable to assess collateral blood flow to the tissue region of interest.

2. A method as recited in claim 1, further comprising:

making a check pulsatility measurement indicative of the volume of blood flow to the tissue region of interest, wherein the check pulsatility measurement is obtained with each of said plurality of arteries substantially occluded.

3. A method as recited in claim 2, further comprising:

comparing said check pulsatility measurement with a check reference range, wherein the obtainment of a check pulsatility measurement within said check reference range is a condition precedent to the obtainment of said second pulsatility measurement.

4. A method as recited in claim 3, further comprising;

utilizing said first pulsatility measurement to determine said check reference range.

5. A method as recited in claim 1, said obtaining step comprising:

passing at least a first light signal through the tissue region of interest;

detecting a portion of said first light signal transmitted through said tissue region of interest; and, using said detected light signal to generate said first pulsatility measurement and said second pulsatility measurement value.

6. A method as recited in claim 5, wherein said using step is performed by a photoplethysmographic device.

7. A method as recited in claim 5, said employing step comprising:

storing said first pulsatility measurement and said second pulsatility measurement for use in the obtainment of a collateral blood flow value.

8. A method as recited in claim 7, wherein said collateral blood flow value is a ratio of the first pulsatility measurement and said second pulsatility measurement.

9. A method as recited in claim 7, further comprising:

outputting said collateral blood flow value to a user.

10. A method as recited in claim 7, wherein said first pulsatility measurement and said second pulsatility measurement are obtained during non-overlapping first and second time periods, respectively, and further comprising:

prompting a user at one or both of the beginning and ending of at least one of said first measurement period and said second measurement period.

11. A method as recited in claim 10, said prompting step comprising:

providing at least one of a visual signal and an audible signal to a user.

12. A method as recited in claim 7, said obtaining step further comprising:

first obtaining a first plurality of pulsatility values; and first determining said first pulsatility measurement utilizing said plurality of pulsatility values.

13. A method as recited in claim 12, said obtaining step further comprising:

second obtaining a second plurality of pulsatility values; and second determining said second pulsatility measurement utilizing said second plurality of pulsatility values.

14. A method as recited in claim 13, said obtaining step further comprising:

first comparing said first plurality of pulsatility values to a first reference range, wherein when all of said first plurality of pulsatility values are within said first reference range said first determining step is completed.

15. A method as recited in claim 14, wherein when any of said first plurality of pulsatility values are outside of said first reference range then first obtaining step is repeated.

16. A method as recited in claim 14, said obtaining step further comprising:

second comparing said second plurality of pulsatility values to a second reference range, wherein when all of said second plurality of pulsatility values are within said second reference range said second determining step is completed.

17. A method as recited in claim 16, wherein when any of said second plurality of pulsatility values are outside of said second reference range then second obtaining step is repeated.

18. A method as recited in claim 16, further comprising:

obtaining a check pulsatility measurement indicative of the volume of blood flow to the tissue region of interest, wherein the check pulsatility measurement is obtained with each of said plurality of arteries substantially occluded; and, comparing said check pulsatility measurement to a check reference range, wherein when said check pulsatility measurement is within said check reference range said second pulsatility measurement is obtained.

19. A method as recited in claim 18, further comprising:

utilizing said first pulsatility measurement to determine said check reference range.

20. A system for use with a photoplethysmographic sensor that provides an output signal indicative of the amount of a light signal transmitted through a tissue region of interest, comprising:

pulsatility means for using said sensor output signal to obtain a first pulsatility measurement and a second pulsatility measurement, wherein said first pulsatility measurement is obtained with a plurality of arteries supplying blood to the tissue region of interest, and wherein said second pulsatility measurement is obtained with at least a selected one of said plurality of arteries substantially occluded; and, collateral flow means for utilizing said first pulsatility measurement and said second pulsatility measurement to compute a collateral blood flow value indicative of collateral blood flow to said tissue region of interest.

21. A system as recited in claim 20, wherein said system is operable in at least a first mode to measure at least one blood analyte concentration value and in a second mode to obtain said collateral blood flow value, and wherein said system further comprises:

a user interface selection means for allowing a user to select one of said first mode and said second mode of operation.

22. A system as recited in claim 20, wherein said user interface is further operable to output said collateral blood flow value to a user.

23. A system as recited in claim 20, wherein said pulsatility means is operable to automatically obtain a first plurality of pulsatility values and to automatically compute said first pulsatility measurement utilizing said first plurality of pulsatility values.

24. A system as recited in claim 23, wherein said pulsatility means is further operable to automatically obtain a second plurality of pulsatility values and to automatically utilize said second plurality of pulsatility values to compute said second pulsatility measurement.

25. A system as recited in claim 24, wherein said pulsatility means is further operable to obtaining a check pulsatility measurement, wherein said check pulsatility measurement is obtained with each of the plurality of arteries substantially occluded, and wherein said pulsatility means obtains said second pulsatility measurement when said check pulsatility measurement is determined to fall within a check reference range.

26. A system as recited in claim 24, wherein said user interface is further operable to provide a series of user output prompts for completing a collateral blood flow test procedure.

27. A system as recited in claim 26, wherein said series of user output prompts comprise instructions for occluding and opening said plurality of arteries in corresponding relation to said obtainment of said first pulsatility measurement, said second pulsatility measurement and said check pulsatility measurement.

* * * * *